US010653610B2

United States Patent
Huynh et al.

(10) Patent No.: US 10,653,610 B2
(45) Date of Patent: May 19, 2020

(54) ESSENTIALLY ANHYDROUS HAIR-TREATMENT COMPOSITIONS COMPRISING A BIS-UREA DERIVATIVE AND SILICA AEROGEL

(71) Applicant: L'OREAL, Paris (FR)

(72) Inventors: Marie Huynh, Monmouth Junction, NJ (US); Anand Mahadeshwar, Scotch Plains, NJ (US); Miao Wang, Westfield, NJ (US); Lisa Chuyin Ye-Tse, Brooklyn, NY (US); Bayle Augustin, Union, NJ (US)

(73) Assignee: L'OREAL, Paris (FR)

( * ) Notice: Subject to any disclaimer, the term of this patent is extended or adjusted under 35 U.S.C. 154(b) by 41 days.

(21) Appl. No.: 15/581,952

(22) Filed: Apr. 28, 2017

(65) Prior Publication Data

US 2018/0311138 A1 Nov. 1, 2018

(51) Int. Cl.
| | | |
|---|---|---|
| A61Q 5/06 | (2006.01) | |
| A61K 8/86 | (2006.01) | |
| A61K 8/58 | (2006.01) | |
| A61K 8/31 | (2006.01) | |
| A61K 8/89 | (2006.01) | |
| A61K 8/37 | (2006.01) | |
| A61Q 5/00 | (2006.01) | |
| A61K 8/02 | (2006.01) | |
| A61K 8/45 | (2006.01) | |
| A61Q 5/12 | (2006.01) | |

(52) U.S. Cl.
CPC .............. *A61K 8/86* (2013.01); *A61K 8/0241* (2013.01); *A61K 8/31* (2013.01); *A61K 8/37* (2013.01); *A61K 8/45* (2013.01); *A61K 8/585* (2013.01); *A61K 8/89* (2013.01); *A61Q 5/00* (2013.01); *A61Q 5/002* (2013.01); *A61Q 5/12* (2013.01); *A61K 2800/31* (2013.01); *A61K 2800/612* (2013.01); *A61Q 5/06* (2013.01)

(58) Field of Classification Search
None
See application file for complete search history.

(56) References Cited

U.S. PATENT DOCUMENTS

| | | | |
|---|---|---|---|
| 6,274,128 B1* | 8/2001 | Bergmann | A61K 8/19 424/400 |
| 8,003,086 B2 | 8/2011 | Chodorowski-Kimmes | |
| 8,668,918 B2* | 3/2014 | Hong | A61K 8/42 424/401 |
| 2007/0098658 A1 | 5/2007 | Chodorowski-Kimmes et al. | |
| 2007/0160635 A1 | 7/2007 | Chodorowski-Kimmes et al. | |
| 2008/0267896 A1 | 10/2008 | Feltin | |
| 2008/0318900 A1 | 12/2008 | Feltin | |
| 2012/0294817 A1* | 11/2012 | Kawaratani | A61Q 1/06 424/64 |
| 2013/0224139 A1 | 8/2013 | Hong et al. | |
| 2015/0007849 A1* | 1/2015 | Cajan | A61Q 5/06 132/203 |
| 2015/0366783 A1* | 12/2015 | Fondin | A61K 8/25 424/70.1 |

FOREIGN PATENT DOCUMENTS

| | | |
|---|---|---|
| WO | WO-2013123324 A1 | 8/2013 |
| WO | WO-2016055751 A1 | 4/2016 |

* cited by examiner

*Primary Examiner* — Jyothsna A Venkat
(74) *Attorney, Agent, or Firm* — Polsinelli PC

(57) ABSTRACT

The instant disclosure relates to anhydrous hair-treatment compositions. The anhydrous hair-treatment compositions typically include one or more bis-urea derivatives, hydrophobic silica aerogel, and one or more solvents, for example, ester oils and non-ester oil solvents. Additional components such as silicones, etc., can also be included. Kits comprising the hair-treatment compositions and methods of using the hair-treatment compositions are also disclosed.

5 Claims, No Drawings

ESSENTIALLY ANHYDROUS HAIR-TREATMENT COMPOSITIONS COMPRISING A BIS-UREA DERIVATIVE AND SILICA AEROGEL

FIELD OF THE DISCLOSURE

The instant disclosure relates to anhydrous (or essentially anhydrous) hair-treatment compositions that can be used when blow-drying and styling hair to provide styling benefits to the hair (e.g. Frizz control, shine, smoothness, etc.) and to protect hair from damage, such as heat damage associated with blow drying and styling hair. The instant disclosure also relates to methods for treating and styling hair using the anhydrous (or essentially anhydrous) hair-treatment compositions.

BACKGROUND

For decades, consumers have used hair styling products to help achieve a desired look, including fuller/thicker hair, sleek and straight hair, and frizz-free defined curls. Many different types of hair styling products are commercially available. Nonetheless, consumers desire new multi-functional hair products that are long lasting, convenient, and impart certain cosmetic characteristics to the hair.

Traditional anhydrous oil treatments have been used to nourish and moisturize dull, dry, and damaged hair. These oil treatments also help control frizz and define hair while maintaining a natural look, but the performance of oil treatments is limited, especially in terms of long lasting shape control. In particular, traditional oil treatments do not typically provide benefits such as shaping memory, improved volume, strengthening, heat protection, etc. Oil treatments moisturize and control frizz while maintaining a natural look, but lack many additional styling benefits that consumers seek.

Styling products that provide styling benefits such as shaping memory, hold, improved volume, etc. are advertised but these products also suffer from certain drawbacks. For example, many styling products provide protection against external factors such as protection from moisture to minimize or reduce frizziness. To protect against moisture, a water-resistant film or coating can be applied to the hair. Many of these films or coatings are formed with film-forming polymers. Depending on the chemical make-up of the film-forming polymers, they may be either soluble in water, or they may be water insoluble polymers that are solubilized in water via various chemical modifications, such as neutralization. Solutions comprising these polymers tend to be viscous, i.e. as the concentration of the polymer increases its viscosity builds up rapidly. Translated to styling applications, as the solvent evaporates, the polymer solution becomes thicker on the hair surface, leaving a sticky or tacky film residue on the hair. This often leaves hair with a stiff and/or "crunchy" feeling (i.e. the films become hard and brittle and therefore have a crunchy feel or sound when manipulated), which is undesirable to many consumers.

Consumers desire new multi-functional hair products that have a natural look and feel, impart good styling benefits to hair, are durable, and lack the drawbacks of other products.

SUMMARY OF THE DISCLOSURE

The instant disclosure relates to anhydrous (or essentially anhydrous) hair-treatment compositions that include a unique combination of components that function to protect hair and to impart desirable cosmetic properties to the hair. For example, the anhydrous (or essentially anhydrous) hair-treatment compositions can be used when blow-drying and styling hair to provide styling benefits such as frizz control, humidity resistance, shine, and smoothness. The compositions also function to protect the hair from damage including heat damage caused by blow dryers and/or hot irons (flat irons, curling irons, etc.). Consumers find the cosmetic properties and the natural look and feel of hair treated with the compositions to be very appealing.

The hair-treatment compositions typically include:
one or more bis-urea derivatives of formula (I):

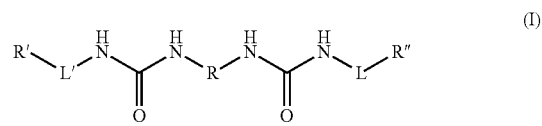

wherein R is a $C_3$-$C_{18}$ linear, branched, or cyclic moiety; and

R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers;

wherein if R' and R" are the same, then both of said groups is selected from the group consisting of α-methyl branched $C_2$-$C_{18}$ ethers and β-methyl branched $C_2$-$C_{18}$ ethers;

wherein L and L' may be same or different and are selected from the group consisting of ethylene oxide chains, propylene oxide chains, and mixtures thereof, and the chains may comprise one or a plurality of repeat units;

hydrophobic silica aerogel; and
one or more solvents.

Additional components including silicones, etc., may also be included. While not wishing to be bound by any particular theory, the inventors believe that the compositions provide the hair with a hydrophobic, flexible, film or film-like coating that is long-lasting, has a very natural look and feel, and improves the styling properties of the hair. The hydrophobic film or film-like coating also provides protection to the hair from damage, for example, heat damage caused by styling techniques (blow drying, heat irons, etc.), and damage caused by environmental stress.

The hair-treatment compositions are unique in their ability to provide hair with improved manageability, long-lasting style and frizz control, and protection. Accordingly, the instant disclosure relates to methods for treating and/or styling hair, for example, methods for improving the manageability of hair, for imparting lasting style and frizz control, and for protecting the hair from damage, including heat damage. The methods typically involve applying an effective amount of a hair-care composition of the instant disclosure to the hair, for instance wet or damp hair, and drying and/or styling the hair, for example, with a blow dryer and/or a heat iron (e.g., flat iron, curling iron, etc.).

DETAILED DESCRIPTION OF THE DISCLOSURE

The term "hair-treatment" composition relates to compositions for application to the hair, characterized by their ability to provide a cosmetic benefit to the hair. For example, benefits may include providing frizz control, smoothness, ease of combability, fullness and body, shine, strengthening, damage repair or resistance to damage, enhancing luster or color, and protection from heat, etc. The hair-treatment compositions are typically anhydrous (or essentially anhydrous) and include:

one or more bis-urea derivatives of formula (I):

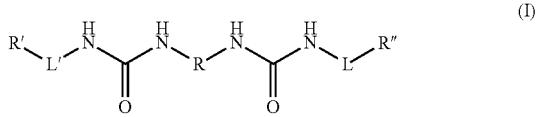

(I)

wherein R is a $C_3$-$C_{18}$ linear, branched, or cyclic moiety; and

R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers;

wherein if R' and R" are the same, then both of said groups is selected from the group consisting of α-methyl branched $C_2$-$C_{18}$ ethers and β-methyl branched $C_2$-$C_{18}$ ethers;

wherein L and L' may be same or different and are selected from the group consisting of ethylene oxide chains, propylene oxide chains, and mixtures thereof, and the chains may comprise one or a plurality of repeat units;

hydrophobic silica aerogel; and one or more solvents.

The total amount of the one or more bis-urea derivatives to the total amount of the hydrophobic silica aerogel may vary but is typically about 1:2 to about 40:1. The total amount of the one or more bis-urea derivatives to the total amount of the hydrophobic silica aerogel may be about 1:1 to about 40:1 or about 1:1 to about 30:1 (bis-urea derivative(s):hydrophobic silica aerogel). Likewise, in some cases, the total amount of the one or more bis-urea derivatives is at least equal to or greater than the total amount of the hydrophobic silica aerogel.

Bis-urea derivatives (such as those described above) and methods for manufacturing the bis-urea derivatives are described in U.S. Pat. No. 8,668,918, which is incorporated herein by reference in its entirety. A non-limiting examples of a useful bis-urea derivative is INCI: Bis-(C12-14 alkyl PPG-4) Hexamethylenediurea, which is commercially available as MILLITHIX MT-800 (Milliken).

The total amount of the one or more bis-urea derivatives can vary but is typically about 0.05 to about 35 wt. %, based on the total weight of the hair-treatment composition. In some cases, the total amount of the one or more bis-urea derivatives is about 0.05 to about 30 wt. %, 0.05 to about 20 wt. %, about 0.05 to about 15 wt. %, about 0.05 to about 12 wt. %, about 0.05 to about 10 wt. %, about 0.05 to about 8 wt. %, about 0.05 to about 5 wt. %, about 0.1 to about 30 wt. %, about 0.1 to about 25 wt. %, about 0.1 to about 20 wt. %, about 0.1 to about 15 wt. %, about 0.1 to about 12 wt. %, about 1 to about 35 wt. %, about 1 to about 30 wt. %, about 1 to about 25 wt. %, about 1 to about 20 wt. %, or about 1 to about 15 wt. %. In some cases, lower total amounts of the one or more bis-urea derivatives may be useful, for example, about 0.01 to about 10 wt. %, about 0.01 to about 8 wt. %, about 0.01 to about 6 wt. %, or about 0.01 to about 5 wt. %.

Silica aerogels are often provided as particles that are typically porous and obtained by replacing (for example, by drying) the liquid component of a silica gel with air. They are typically synthesized via a sol-gel process in a liquid medium and then dried, usually by extraction with a supercritical fluid; the most commonly used being supercritical $CO_2$. This type of drying makes it possible to avoid shrinkage of the pores and of the material. The sol-gel process and the various drying operations are described in detail in Brinker C. J. and Scherer G. W., Sol-Gel Science, New York (Academic Press, 1990), which is incorporated herein by reference in its entirety. The particles, however, when added to a solvent are dissolved and therefore do not exist as particles in the final hair-treatment composition.

Hydrophobic silica aerogels include those that exhibit a specific surface area per unit of mass (SM) ranging from 500 to 1500 $m^2/g$, from 600 to 1200 $m^2/g$, or 600 to 800 $m^2/g$, and a size, expressed as the volume-mean diameter (D[0.5]), ranging from 1 to 1500 μm, from 1 to 1000 μm, or from 1 to 100 μm, in particular from 1 to 30 μm, from 5 to 25 μm, or from 5 to 20 μm, and in some cases from 5 to 15 μm.

In some cases, the hydrophobic silica aerogel is provided in the form of particles that have a size, expressed as the volume-mean diameter (D[0.5]), ranging from 1 to 30 μm, from 5 to 25 μm, from 5 to 20 μm, or from 5 to 15 μm. Additionally, the hydrophobic silica aerogel particles can have a specific surface area per unit of mass (SM) ranging from 600 to 800 $m^2/g$ and a size expressed as the volume-mean diameter (D[0.5]) ranging from 5 to 20 μm or from 5 to 15 μm. Moreover, the hydrophobic silica aerogel particles may have a specific surface area per unit of volume SV ranging from 5 to 100 $m^2/cm^3$, from 10 to 90 $m^2/cm^3$, from 15 to 40 $m^2/cm^3$, from 20 to 85 $m^2/cm^3$, or from 24 to 80 $m^2/cm^3$. The hydrophobic silica aerogel particles may have an oil-absorbing capacity, measured at the wet point, ranging from 5 to 18 ml/g, from 6 to 15 ml/g, or from 8 to 12 ml/g.

In some instances, particularly useful hydrophobic silica aerogel particles include silylated silica (INCI name: silica silylate), sold under the name VM-2270 by the company Dow Corning, the particles having an average size ranging from 5-15 microns and a specific surface area per unit of mass ranging from 600 to 800 $m^2/g$.

The total amount of the hydrophobic silica aerogel in the hair-treatment compositions may vary but is typically about 0.01 to about 10 wt. %, based on the total weight of the hair-treatment composition. The total amount of the hydrophobic silica aerogel may be about 0.01 to about 9 wt. %, about 0.01 to about 8 wt. %, about 0.01 to about 7 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, or about 0.1 to about 2 wt. %.

Many solvents appropriate for use in anhydrous (or essentially anhydrous) compositions are known. Non-limiting examples of solvents include oils, waxes, butters, alkanes, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, ceramide, and a mixture thereof.

The total amount of the one or more solvents may vary but is typically about 50 wt. % to about 99.5 wt. %, based on the total amount of the hair-treatment composition. The total amount of the one or more solvents may be about 55 to about 99.5 wt. %, about 60 to about 99.5 wt. %, or about 65 to about 99.5 wt. %.

In some cases, the one or more solvents include one or more oils (ester oils, vegetable oils, animal oils, non-ester oils, fluoro oils, hydrocarbon-based oils, and a mixture thereof). One or more ester-oils are particularly useful in some instances. For examples, esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used. Non-limiting examples of ester-oils include: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis (2-ethylhexyl) maleate; tri isopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate, and a mixture thereof.

Ester oils also include sugar esters and diesters of $C_6$-$C_{30}$ and preferably $C_{12}$-$C_{22}$ fatty acids. The term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides. Examples of suitable sugars that may be mentioned include sucrose (or saccharose), glucose, galactose, ribose, fructose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds. The esters according to this variant may also be selected from monoesters, diesters, triesters, tetraesters and polyesters, and mixtures thereof. These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters, as well as pentaerythrityl tetraethyl hexanoate.

Further non-limiting examples of ester oils include diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isononyl isononanoate, ethylhexyl palmitate, $C_{12}$-$C_{15}$ alkyl benzoate isodecyl oleate, glyceryl tri(2-ethylhexanoate), pentaerythrithyl tetra(2-ethyl hexanoate), 2-ethylhexyl succinate, diethyl sebacate, and mixtures thereof. In some cases, the one or more ester-oils are selected from the group consisting of isopropyl myristate, isononyl isononanoate, ethylhexyl palmitate, $C_{12}$-$C_{15}$ alkyl benzoate, and a mixture thereof.

All of the one or more solvents may be ester-oils or only a portion of the one or more solvents may be ester-oils. Accordingly, the total amount of the one or more ester-oils (regardless of whether additional non-ester oil solvents are present) is about 50 to about 99.5 wt. %, based on the total weight of the hair-treatment composition. The total amount of the one or more ester-oils may be about 55 to about 99.5 wt. %, about 60 to about 99.5 wt. %, or about 65 to about 99.5 wt. %, about 50 to about 99 wt. %, about 55 to about 99 wt. %, about 60 to about 99 wt. %, about 65 to about 99 wt. %, about 50 to about 90 wt. %, about 60 to about 90 wt. %, or about 60 to about 80 wt. %.

In some cases, the hair-treatment compositions include one or more solvents other than (or in addition to) the one or more ester-oils. In some cases, the hair-treatment compositions may include one or more solvents that are non-ester oils. For example, the hair-treatment compositions may include one or more non-ester oils selected from the group consisting of linear, branched and/or cyclic alkanes. Non-limiting examples include paraffins, isoparaffins, petroleum jelly, hydrogenated polyisobutylene, isododecane, and a mixture thereof.

The total amount of the one or more non-ester oils (regardless of whether the composition includes ester-oils) may vary but it typically about 0.1 to about 40 wt. %, based on the total weight of the hair-treatment composition. The total amount of the one or more non-ester oils may be about 0.1 to about 30 wt. %, about 0.1 to about 20 wt. %, about 0.1 to about 15 wt. %, about 0.1 to about 10 wt. %, about 1 to about 40 wt. %, about 1 to about 30 wt. %, about 1 to about 20 wt. %, about 1 to about 15 wt. %, or about 1 to about 10 wt. %.

One or more silicones may be included in the hair-treatment compositions. Non-limiting examples of silicones include polyorganosiloxanes, polyalkylsiloxanes, polyarylsiloxanes, polyalkarylsiloxanes, polyestersiloxanes, and a mixture thereof. In particular, suitable examples of silicones include dimethicone, cyclomethicone, amodimethicone, trimethyl silyl amodimethicone, phenyl trimethicone, trimethyl siloxy silicate, and mixtures thereof. In some cases, the hair-treatment compositions include one or more cyclic silicones, one or more polysilsesquioxanes, or a mixture thereof.

Exemplary cyclic silicones include, without limitation, those having 3 to 6, or 3 to 4 or 3 to 5, (or any of 3, 4, 5, or 6) Si—O groups in the cyclic backbone chain (e.g., siloxanes). Exemplary cyclic silicones include, without limitation, cyclomethicone, cyclotetrasiloxane, cyclopentasiloxane (e.g., Cyclomethicone 5-NF), cyclohexasiloxane, and a mixture of cyclohexasiloxane and cyclopenasiloxane (e.g., DOW CORNING 246 Fluid (d6+d5)). Silsesquioxane compounds (sometimes referred to as silsesquioxane resins) may also be included in the hair-treatment compositions. For example, in some cases, the hair-treatment compositions may include a polysilsesquioxanes such as, for example, polymethylsilsesquioxane, polypropylsilsesquioxane, polyphenylsilsesquioxane, etc., and a mixture thereof. In some cases, the hair-treatment compositions may include cyclohexasiloxane and/or polypropylsilsesquioxane.

A more exhaustive list of silicones that may be included in the hair-treatment compositions is provided later, under the heading "Silicones."

The total amount of the one or more silicones may vary but is typically about 0.01 to about 60 wt. %, based on the total weight of the hair-treatment composition. In some cases, the total amount of the one or more silicones is about 0.01 to about 50 wt. %, about 0.01 to about 40 wt. %, about 0.01 to about 30 wt. %, about 0.1 to about 60 wt. %, about 0.1 to about 50 wt. %, about 0.1 to about 40 wt. %, about 0.1 to about 30 wt. %, about 0.5 to about 50 wt. %, about 0.5 to about 40 wt. %, about 0.5 to about 30 wt. %.

In one embodiment, the hair-treatment compositions of the instant case relate to an anhydrous (or essentially anhydrous) hair-treatment composition comprising:

about 0.01 to about 15 wt. %, about 0.1 to about 15 wt. %, or about 0.1 to about 10 wt. % of BIS-(C12-14 alkyl PPG-4) hexamethylenediurea;

about 0.01 to about 10 wt. %, about 0.1 to about 8 wt. %, or about 0.1 to about 5 wt. % of silica silylate; and about 50 to about 99.5 wt. %, about 55 to about 99.5 wt. %, or about 60 to about 99.5 wt. % of one or more ester oils, for example, C12-15 alkyl benzoate, isopropyl myristate, ethylhexyl palmitate, isononyl isononanoate, or a mixture thereof.

In another embodiment, the hair-treatment compositions of the instant case relate to an anhydrous (or essentially anhydrous) hair-treatment composition comprising:

about 0.01 to about 15 wt. %, about 0.1 to about 15 wt. %, or about 0.1 to about 10 wt. % of BIS-(C12-14 alkyl PPG-4) hexamethylenediurea;

about 0.01 to about 10 wt. %, about 0.1 to about 8 wt. %, or about 0.1 to about 5 wt. % of silica silylate;

about 50 to about 99.5 wt. %, about 55 to about 99.5 wt. %, or about 60 to about 99.5 wt. % of one or more ester oils, for example, C12-15 alkyl benzoate, isopropyl myristate, ethylhexyl palmitate, isononyl isononanoate, or a mixture thereof;

about 0.1 to about 15 wt. %, about 0.1 to about 10 wt. %, or about 1 to about 10 wt. % of one or more non-ester oils, for example one or more non-ester oils selected from the group consisting of linear, branched and/or cyclic alkanes, in particular, isododecane; and about 0.1 to about 40 wt. %, about 0.1 to about 30, or about 1 to about 30 wt. % of one or more silicones, for example one or more silicones selected from the group consisting of polyorganosiloxanes, polyalkylsiloxanes, polyarylsiloxanes, polyalkarylsiloxanes, polyestersiloxanes, alkylmethylsilicone polyether copolymers, and a mixture thereof, in particular, cyclohexasiloxane, polypropylsilsesquixane, and a mixture thereof.

The hair-treatment compositions may be packaged in a variety of different containers, such as, for example, a ready-to-use container. Non-limiting examples of useful packaging include tubes, jars, caps, unit dose packages, and bottles, including squeezable tubes and bottles. The hair-treatment compositions may in a variety of different forms. For example, the compositions may be a solid, including a molded or shaped solid, a foam, a gel, a cream, a wax, a paste, pomade, a mousse, a spray, a serum, an aerosol, a lotion, etc. In some instances, solid compositions are useful. The solid compositions include solid compositions that are molded or shaped. For example, the solid composition may be in the form of a stick and packaged in an applicator similar to how lipstick and/or deodorant is shaped and packaged. The solid composition may have a melting point of at least 60° C., of at least 65° C., of at least 70° C., or of at least 75° C. Solid hair-treatment compositions can be useful because they are particularly stable and easy to use.

The hair-treatment compositions can be used in a professional salon or at home during an individual's regular hair-care routine. Use of the hair-treatment compositions does not require special procedures that are only available at professional salons. As mentioned previously, the hair-treatment compositions are unique in their ability to provide hair with improved manageability, long-lasting style and frizz control, and protection. Accordingly, the instant disclosure relates to methods for treating and/or styling hair, for example, methods for improving the manageability of hair, for imparting lasting style and frizz control, and for protecting the hair from damage, including heat damage. The methods typically involve applying an effective amount of a hair-care composition according to the instant disclosure to the hair, for instance wet or damp hair, and drying and/or styling the hair, for example, with a blow dryer and/or a heat iron (e.g., flat iron, curling iron, etc.). The hair-care composition may be applied to wet or damp hair that has been freshly washed and/or optionally conditioned.

Methods for treating the hair include:
imparting smoothness and/or shine to the hair;
providing curl definition to the hair;
strengthening hair fibers and/or minimizing/preventing breakage;
providing frizz control to the hair;
protecting the hair from heat damage;
increasing the appearance of hair volume;
improving the texture and/or tactile properties of the hair; and
improving the grip and/or adhesion properties of the hair (e.g., improving the ability of the hair to hold to and/or grip a brush without slipping away from the brush during drying and/or styling).

The hair-treatment compositions can "treat" the hair by imparting a desirable cosmetic property to the hair, such as any one of those outlined above. For example, the hair-treatment compositions are useful in methods for styling hair. Methods for styling hair may include applying a hair-treatment composition to hair and subsequently styling the hair, without first rinsing the hair-treatment composition from the hair (using the composition as a leave-in hair-styling product). The hair-treatment composition may be applied to freshly washed and/or conditioned hair that remains wet or damp from the washing and/or conditioning process (e.g., within about 5, 10, 15, or 30 minutes from rinsing a shampoo and/or a conditioner from the hair). The hair-treatment composition may be massaged onto/into hair fibers and the hair subsequently dried and styled. For instance, the hair may be dried using a hair dryer and/or may be styled using a heat iron (e.g., a straight iron, curling iron, etc.). Not only do the hair-treatment compositions provide styling benefits such as smoothness and shine, but the compositions also protect the hair during the styling process from heat. Furthermore, wet or damp hair treated with the hair-treatment compositions and subsequently dried, was perceived by users as drying quickly.

More exhaustive but non-limiting lists of components useful in the hair-treatment compositions disclosed herein are provided below.

Bis-Urea Derivatives

Bis-urea derivatives useful in the instant hair-treatment compositions include those of the following formula:

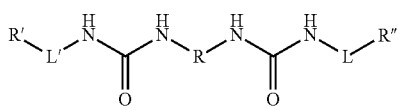

wherein R is a $C_3$-$C_{18}$ linear, branched, or cyclic moiety; and R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers, wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof.

In some instances, the bis-urea derivatives may include those of the following formula:

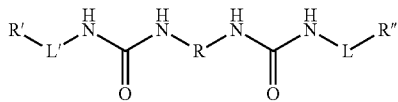

wherein R is a $C_3$-$C_{18}$ linear or branched alkylene chain or an aromatic ring; and R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers; wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof, and the chains may comprise one or a plurality of repeat units.

In some instances, the bis-urea derivatives may include those of the following formula:

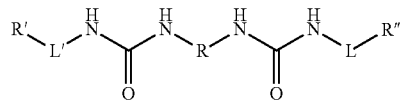

wherein R is a $C_3$-$C_{18}$ linear, branched or cyclic moiety selected from the group consisting of unsubstituted or substituted phenyl, phenyl ether, and phenyl methylene; and R' and R" may be the same or different and are selected from the group consisting of $C_1$-$C_{36}$ linear or branched alkanes, α-methyl branched $C_2$-$C_{36}$ alkanes or aryl alkanes, α-methyl branched $C_2$-$C_{36}$ ethers, β-methyl branched $C_2$-$C_{36}$ alkanes, and β-methyl branched $C_2$-$C_{36}$ ethers; wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof, and the chains may comprise one or a plurality of repeat units.

In particular, the bis-urea derivative may be a compound of the following formula:

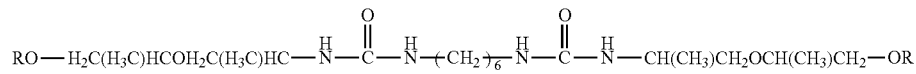

wherein R is a $C_1$-$C_{36}$ linear or branched alkane, a $C_6$-$C_{24}$ linear or branched alkane, or a $C_{10}$-$C_{16}$ linear or branched alkane. A non-limiting example of a bis-urea derivative, such as those described above is as follows:

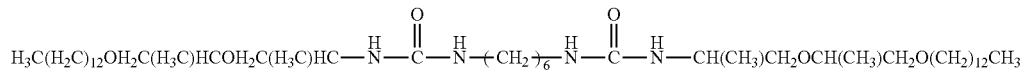

Bis-urea derivatives (such as those described above) and methods for manufacturing the bis-urea derivatives are described in U.S. Pat. No. 8,668,918, which is incorporated herein by reference in its entirety. INCI: Bis-(C12-14 alkyl PPG-4) Hexamethylenediurea is commercially available as Millithix® MT-800 (Milliken).

Hydrophobic Silica Aerogel

Hydrophobic silica aerogels are often provided in the form of particles, porous material obtained by replacing (by drying) the liquid component of a silica gel with air. They are generally synthesized via a sol-gel process in a liquid medium and then dried, usually by extraction with a supercritical fluid; the one most commonly used being supercritical $CO_2$. This type of drying makes it possible to avoid shrinkage of the pores and of the material. The sol-gel process and the various drying operations are described in detail in Brinker C. J. and Scherer G. W., Sol-Gel Science, New York, Academic Press, 1990. When combined with solvents, however, the particles dissolve.

Hydrophobic silica aerogels include those that exhibit a specific surface area per unit of mass (SM) ranging from 500 to 1500 $m^2/g$, from 600 to 1200 $m^2/g$, or 600 to 800 $m^2/g$, and a size, expressed as the volume-mean diameter (D[0.5]), ranging from 1 to 1500 µm, from 1 to 1000 µm, or from 1 to 100 µm, in particular from 1 to 30 µm, from 5 to 25 µm, or from 5 to 20 µm, and in some cases from 5 to 15 µm.

In some cases, the hydrophobic silica aerogel particles used in the present invention have a size, expressed as the volume-mean diameter (D[0.5]), ranging from 1 to 30 µm, from 5 to 25 µm, from 5 to 20 µm or from 5 to 15 µm.

The specific surface area per unit of mass can be determined by the nitrogen absorption method, known as the BET (Brunauer-Emmett-Teller) method, described in The Journal of the American Chemical Society, Vol. 60, page 309, February 1938 and corresponding to the international standard ISO 5794/1 (appendix D). The BET specific surface area corresponds to the total specific surface area of the particles under consideration.

The sizes of the silica aerogel particles can be measured by static light scattering using a commercial particle size analyzer of MasterSizer 2000 type from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, H. C., "Light Scattering by Small Particles", Chapters 9 and 10, Wiley, New York, 1957.

In some instances, the hydrophobic silica aerogel particles have a specific surface area per unit of mass (SM) ranging from 600 to 800 $m^2/g$ and a size expressed as the volume-mean diameter (D[0.5]) ranging from 5 to 20 µm or from 5 to 15 µm.

The silica aerogel particles may advantageously have a tapped density ρ ranging from 0.02 $g/cm^3$ to 0.10 $g/cm^3$, from 0.03 $g/cm^3$ to 0.10 $g/cm^3$, from 0.04 $g/cm^3$ to 0.10 $g/cm^3$, or from 0.05 $g/cm^3$ to 0.08 $g/cm^3$. The density ρ, known as the tapped density, may be assessed according to the following protocol: 40 g of powder are poured into a measuring cylinder; the measuring cylinder is then placed on a Stay 2003 machine from Stampf Volumeter; the measuring cylinder is then subjected to a series of 2500 packing motions (this operation is repeated until the difference in volume between two consecutive tests is less than 2 percent); the final volume Vf of packed powder is then measured directly on the measuring cylinder. The tapped density is determined by the ratio w/Vf, in this instance 40/Vf (Vf being expressed in $cm^3$ and w in g).

In some cases, the hydrophobic silica aerogel particles may have a specific surface area per unit of volume SV ranging from 5 to 100 $m^2/cm^3$, from 10 to 90 $m^2/cm^3$, from 15 to 40 $m^2/cm^3$, from 20 to 85 $m^2/cm^3$, or from 24 to 80 $m^2/cm^3$. The specific surface area per unit of volume is given by the relationship: $S_V = S_M \times \rho$, where ρ is the tapped density, expressed in $g/cm^3$, and $S_M$ is the specific surface area per unit of weight, expressed in $m^2/g$, as defined above.

The hydrophobic silica aerogel particles may have an oil-absorbing capacity, measured at the wet point, ranging from 5 to 18 ml/g, from 6 to 15 ml/g, or from 8 to 12 ml/g. The absorption capacity measured at the wet point, denoted Wp, corresponds to the amount of oil which it is necessary to add to 100 g of particles in order to obtain a homogeneous paste. It is measured according to the "wet point" method or method of determination of oil uptake of a powder described in the standard NF T 30-022. It corresponds to the amount of oil adsorbed onto the available surface of the powder and/or absorbed by the powder by measurement of the wet point, described below:

An amount m=2 g of powder is placed on a glass plate and the oil (isononyl isononanoate) is then added dropwise. After addition of 4 to 5 drops of oil to the powder, mixing is performed using a spatula, and addition of oil is continued until conglomerates of oil and powder have formed. From this point, the oil is added at the rate of one drop at a time and the mixture is subsequently triturated with the spatula. The addition of oil is stopped when a firm and smooth paste is obtained. This paste must be able to be spread over the glass plate without cracks or the formation of lumps. The volume Vs (expressed in ml) of oil used is then noted. The oil uptake corresponds to the ratio Vs/m.

In some cases, particularly useful hydrophobic silica aerogel particles are silylated silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles modified at the surface by silylation, reference may be made U.S. Pat. No. 7,470,725, incorporated herein by reference in its entirety.

In some cases, particularly useful hydrophobic silica aerogel particles are surface-modified with trimethylsilyl groups. Mention may be made, as hydrophobic silica aerogels which can be used in the invention, for example, of the aerogel sold under the name VM-2260 (INCI name: Silica silylate) by Dow Corning, the particles of which have a mean size of approximately 1000 microns and a specific surface area per unit of mass ranging from 600 to 800 $m^2/g$. Mention may also be made of the aerogels sold by Cabot under the references Aerogel TLD 201, Aerogel OGD 201, Aerogel TLD 203, Enova® Aerogel MT 1100 and Enova Aerogel MT 1200.

In some cases, particularly useful hydrophobic silica aerogel particles are those sold under the name VM-2270 (INCI name: Silica silylate), by the company Dow Corning, the particles having an average size ranging from 5-15 microns and a specific surface area per unit of mass ranging from 600 to 800 $m^2/g$.

Solvents

The solvents are typically hydrophobic and/or non-polar. Examples of suitable solvents include, but are not limited to, oils, mineral oils, solvents, base oils, synthetic hydrocarbons, solid hydrocarbons, semi-solid hydrocarbons, waxes, petroleum distillates, petrolatums, and a mixture thereof. In some instances, the diluent may include paraffinic or naphthenic oil.

Non-limiting examples of solvents include a diglyceride, a PPG alkyl ether, a therapeutic oil, acetylated lanolin alcohol, alexandria laurel tree oil, alkyl benzoate, alkyl octanoate, almond oil, an essential oil, an unsaturated or polyunsaturated oil, apricot stone oil, arachidyl behenate, arachidyl propionate, avocado oil, barley oil, basil oil, beeswax, benzyl laurate, benzyl myristate, benzyl palmitate, bis(octyldodecyl stearoyl) dimer dilinoleate, *borage* seed oil, butyl myristate, butyl stearate, C12-C15 alkyl benzoate, C12-C15 alkyl octanoate, calendula oil, camphor oil, canelle nut tree oil, canola oil, capric/caprylic triglycerides, caprylic/capric triglyceride castor oil, cardamom oil, carrot oil, castor oil, cetearyl ethylhexanoate, cetearyl isononanoate, cetearyl octanoate, cetyl acetate, cetyl ethylhexanoate, cetyl lactate, cetyl myristate, cetyl octanoate, cetyl palmitate, cetyl ricinoleate, citronella oil, clary sage oil, clove oil, cocoglycerides, coconut oil, cod-liver oil, corn oil, cotton oil, cottonseed oil, cypress oil, decyl oleate, diethyleneglycol diethylhexanoate, diethyleneglycol diisononanoate, diethyleneglycol dioctanoate, diethylhexanoate, diethylhexyl adipate, diethylhexyl malate, diethylhexyl succinate, diisopropyl adipate, diisopropyl dimerate, diisopropyl sebacate, diisosteary dimer dilinoleate, diisostearyl fumerate, dioctyl malate, dioctyl sebacate, disopropyl adipate, dodecyl oleate, essential oils, ester derivatives of lanolic acid, ester oils, ethylhexyl cocoate, ethylhexyl ethyl hexanoate, ethylhexyl hydroxystarate, ethylhexyl isononanoate, ethylhexyl palmitate, ethylhexyl palmytate, ethylhexyl pelargonate, ethylhexyl stearate, evening primrose oil, flaxseed oil, frankincense oil, gelled mineral oil, ginger oil, glycereth triacetate, glycerol triheptanoate, glyceryl oleate, glyceryl trioctanoate, glyceryl triundecanoate, grape seed oil, grapefruit oil, groundnut oil, hard fat, hazelnut oil, heavy mineral oil, hempseed oil, herring oil, hexadecyl stearate, hexyl laurate, hydrocarbon oils, hydrogenated castor oil, hyssop oil, isoamyl laurate, isocetearyl octanoate, isocetyl isocetyl behenate, isocetyl lanolate, isocetyl palmitate, isocetyl salicylate, isocetyl stearate, isocetyl stearoyl stearate, isodecyl ethylhexanoate, isodecyl isononanoate, isodecyl oleate, isododecane, isohexadecane isododecane, isohexadecanol, isohexyl decanoate, isononyl isononanoate, isononyl octanoate, isoparaffin, isopropyl isostearate, isopropyl lanolate, isopropyl laurate, isopropyl myristate, isopropyl palmitate, isopropyl stearate, isosteary citrate, isosteary salicylate, isosteary tartarate, isostearyl behenate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isotridecyl isononanoate, jasmine oil, jojoba oil, lauryl lactate, lavender oil, lemon oil, light mineral oil, liquid paraffin, liquid triglycerides, lucerne oil, maize germ oil, maleated soybean oil, mandarin oil, manuka oil, marjoram oil, marrow oil, MCT oil, millet oil, mineral oil, myristyl lactate, myristyl myristate, myristyl neopentanoate, myristyl propionate, myrrh oil, neopentylglycol dicaprate, neopentylglycol dicaprylate/dicaprate, neroli oil, nutmeg oil, octyl palmitate, octyl stearate, octyldodecanol, octyldodecyl behenate, octyldodecyl hydroxystearate, octyldodecyl myristate, octyldodecyl stearoyl stearate, oils from animal origin, oils of plant origin, oleyl erucate, oleyl lactate, oleyl oleate, olive oil, palm oil, passionflower oil, peanut oil, pentaerythrityl tetrastearate, petitgrain oil, petrolatum, polyisobutylene, polyolefin, poppy oil, PPG alkyl ethers, PPG-10 cetyl ether, PPG-10 oleyl ether, PPG-11 stearyl ether, PPG-12 butyl ether, PPG-14 butyl ether, PPG-15 butyl ether, PPG-15 stearyl ether, PPG-16 butyl ether, PPG-17 butyl ether, PPG-18 butyl ether, PPG-2 butyl ether, PPG-2 methyl ether, PPG-20 butyl ether, PPG-20 oleyl ether, PPG-22 butyl ether, PPG-23 oleyl ether, PPG-24 butyl ether, PPG-26 butyl ether, PPG-28 cetyl ether, PPG-3 methyl ether, PPG-3 myristyl ether, PPG-30 butyl ether, PPG-30 cetyl ether, PPG-30 isocetyl ether, PPG-30 oleyl ether, PPG-33 butyl ether, PPG-37 oleyl ether, PPG-4 butyl ether, PPG-4 lauryl ether, PPG-4 myristyl ether, PPG-40 butyl ether, PPG-5 butyl ether, PPG-50 cetyl ether, PPG-50 oleyl ether, PPG-52 butyl ether, PPG-53 butyl ether, PPG-7 lauryl ether, PPG-9 butyl ether, PPG-9-13 butyl ether, propyl myristate, propylene glycol dicaprate, propylene glycol dicaprylate, propylene glycol myristyl ether acetate, propylene glycol ricinoleate, rapeseed oil, rosehip oil, rye oil, safflower oil, sage oil, salmon oil, sesame oil, shea butter, soya oil, soybean oil, stearyl caprate, stearyl heptanoate, stearyl propionate, sunflower oil, sweet almond oil, synthetic isoalkane, sysymbrium oil, syzigium aromaticum oil, tangerine oil, tea tree oil, therapeutic oils, tocopheryl acetate, tocopheryl linoleate, tridecyl ethylhexanoate, tridecyl isononanoate, triisocetyl citrate, unsaturated or polyunsaturated oils, vanilla oil, verbena oil, walnut oil, wheat germ glycerides, wheat germ oil, white petrolatum and mixtures thereof.

Examples of suitable commercially available hydrophobic, non-polar solvents include, but are not limited to EXCEL 260-HC which is available from Excel Paralubes; ISOPAR L, ISOPAR M, and ISOPAR V which are available from Exxon Chemical; DRAKEOL 7, DRAKEOL 31, DRAKEOL 34, Snow White Petrolatum, and Amber Petrolatum which are available from Penreco; CONOSOL C145, CONOSOL 200, CONOSOL 260, and CONOSOL V 340 which are available from Conoco, Inc.; PERMETHYL 99A, PERMETHYL 101A, and PERMETHYL 102A which are available from Presperse; and PANALANE L14E which is available from Amoco.

In some instances, the diluent may be selected from the group consisting of oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. For instance, one or more fatty compounds may be selected from the group consisting of glycol distearate, PEG-55 propylene glycol oleate, cetearyl alcohol, soybean oil, cetyl esters, isopropyl myristate, cetearyl alcohol, orbigynya oleifera seed oil, propylene glycol dicaprylate/dicaprate, mineral oil, and a mixture thereof.

Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting olyglycerol esters of fatty acids include those of the following formula:

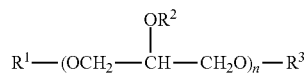

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, glyceryl monomyristate, glyceryl monopalmitate, glyceryl monostearate, glyceryl isostearate, glyceryl monooleate, glyceryl ester of mono(olive oil fatty acid), glyceryl dioleate and glyceryl distearate. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and a mixture thereof.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the diluent may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Nonlimiting examples of the high melting point compounds are found in International Cosmetic Ingredient Dictionary, Fifteenth Edition, 2014, which is incorporated herein by reference in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are cetyl alcohol, stearyl alcohol and mixtures thereof.

Ester Oils

Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may be made of: diethyl sebacate; isopropyl lauroyl sarcosinate; diisopropyl sebacate; bis(2-ethylhexyl)

sebacate; diisopropyl adipate; di-n-propyl adipate; dioctyl adipate; bis(2-ethylhexyl) adipate; diisostearyl adipate; bis (2-ethylhexyl) maleate; tri isopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. The term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides. Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds. The esters according to this variant may also be selected from monoesters, diesters, triesters, tetraesters and polyesters, and mixtures thereof. These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters, as well as pentaerythrityl tetraethyl hexanoate.

More particularly, use is made of monoesters and diesters and especially sucrose, glucose or methylglucose monooleates or dioleates, stearates, behenates, oleopalmitates, linoleates, linolenates and oleostearates.

As examples of non-limiting ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethyl hexanoate), 2-ethylhexyl succinate, diethyl sebacate, and mixtures thereof.

Vegetable Oils

As used herein the term "vegetable" is interpreted broadly so that it encompasses all plants of the kingdom Plantae. Non-limiting examples of vegetable oils include coconut oil, Corn oil, Cottonseed oil, Olive oil, Palm oil, Peanut oil Rapeseed oil, Safflower oil, Sesame oil, Soybean oil, and Sunflower oil. Non-limiting examples of nut-derived vegetable oils include Hazelnut oil, Almond oil, Beech nut oil, Brazil nut oil, Extra virgin oil, Cashew oil, Macadamia oil, Mongongo nut oil (or manketti oil), Pecan oil, Pine nut oil, Pistachio oil, and Walnut oil. Non-limiting examples of citrus oil include Grapefruit seed oil, Lemon oil, Orange oil. Non-limiting examples of oils from melon and gourd seeds include Watermelon seed oil, Bitter gourd oil, Bottle gourd oil, Buffalo gourd oil, Butternut squash seed oil, *Egusi* seed oil, Pumpkin seed oil. Additional non-limiting examples of oils include *Borage* seed oil, blackcurrant seed oil, and evening primrose oil, which all have a significant amount of gamma-Linolenic acid (GLA), Açaí oil, Black seed oil, Blackcurrant seed oil, *Borage* seed oil, Evening primrose oil, Flaxseed oil (called linseed oil when used as a drying oil), Amaranth oil, Apricot oil, Apple seed oil, *Argan* oil, Avocado oil, *Babassu* oil, Ben oil, Borneo tallow nut oil, Cape chestnut oil, Carob pod oil (*Algaroba* oil), Cocoa butter, Cocklebur oil, Cohune oil, Coriander seed oil, Date seed oil, Dika oil, False flax oil made of the seeds of *Camelina sativa*, Grape seed oil, Hemp oil, Kapok seed oil, Kenaf seed oil, *Lallemantia* oil, Mafura oil, Marula oil, Meadowfoam seed oil, Mustard oil (pressed), poppyseed oil, Okra seed oil, Papaya seed oil, *Perilla* seed oil, Persimmon seed oil, Pequi oil, Pili nut oil, Pomegranate seed oil, and Pracaxi oil.

Non-Ester Oils

The at least one non-ester oil may be chosen from natural, synthetic, saturated and unsaturated oils, including mineral oils. Mention may be made of linear, branched and/or cyclic alkanes which may be volatile and, in particular, liquid paraffin, liquid petroleum jelly or hydrogenated polyisobutylene, isododecane or "Isopars", and volatile isoparaffins.

Mention may also be made of aliphatic fatty liquid monoalcohols containing 6 to 40 carbon atoms, the hydrocarbon-based chain not comprising a substitution group. Monoalcohols according to the invention that may be mentioned include oleyl alcohol, decanol, octyldodecanol and linoleyl alcohol.

Mention may also be made of silicone oils such as polydimethylsiloxanes and polymethylphenylsiloxanes, optionally substituted with aliphatic and/or aromatic groups, which are optionally fluorinated, or with functional groups such as hydroxyl, thiol and/or amine groups, and volatile silicone oils, which are especially cyclic.

In particular, mention may be made of volatile and/or non-volatile, optionally branched silicone oils. The term "volatile oil" means oil capable of evaporating from the skin or the lips in less than one hour, and especially having a vapor pressure, at room temperature and atmospheric pressure, ranging from $10^{-3}$ to 300 mmHg (0.13 Pa to 40,000 Pa).

As volatile silicone oils, mention may be made of linear or cyclic silicones containing from 2 to 7 silicon atoms, these silicones optionally comprising alkyl or alkoxy groups containing from 1 to 10 carbon atoms. Mention may be made in particular of octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane and decamethyltetrasiloxane, and mixtures thereof.

Among the non-volatile silicone oils that may be mentioned are non-volatile polydialkylsiloxanes, such as non-volatile polydimethylsiloxanes (PDMS); polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyl trimethyl-siloxy diphenylsiloxanes, diphenyl dimethicones, diphenyl methyldiphenyltrisiloxanes and polymethyl-phenylsiloxanes; polysiloxanes modified with fatty acids (especially of $C_8$-$C_{20}$), fatty alcohols (especially of $C_8$-$C_{20}$) or polyoxyalkylenes (especially polyoxy-ethylene and/or polyoxypropylene); amino polysiloxanes; polysiloxanes containing hydroxyl groups; fluoro poly-siloxanes comprising a fluorinated group that is pendent or at the end of a silicone chain, containing from 1 to 12 carbon atoms, all or some of the hydrogen atoms of which are replaced with fluorine atoms; and mixtures thereof.

Fluoro Oils

The cosmetic compositions described herein may comprise one or more fluoro oils. For example, the one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The cosmetic compositions described herein may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the compositions include a synthetic oil selected from the group consisting of hydrogenated polyisobutene and hydrogenated polydecene.

The hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is 10, for instance Purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC® by Cognis;

(viii) fatty amides, such as isopropyl N-lauroyl sarcosinate, such as the product sold under the trade name Eldew SL 205® from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In certain instances, the non-volatile hydrocarbon-based oils are glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, such as octyldodecanol.

As volatile hydrocarbon-based oils, mention is made of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4, 6-pentamethylheptane), isodecane or isohexadecane, the oils sold under the Isopar or Permethyl trade names, branched C $C_8$-$C_{16}$ esters, and isohexyl neopentanoate.

Silicones

Exemplary silicones include, without limitation, cyclic silicones, such as those having 3 to 6, or 3 to 4 or 3 to 5, (or any of 3, 4, 5, or 6) Si—O groups in the cyclic backbone chain (e.g., siloxanes). In some cases, the cyclic silicone is a volatile silicone. In some cases, the cyclic silicone is a low viscosity silicone. Exemplary cyclic silicones include, without limitation, cyclomethicone, cyclotetrasiloxane, cyclopentasiloxane (e.g., Cyclomethicone 5-NF), cyclohexasiloxane and a mixture of cyclohexasiloxane and cyclopenasiloxane (e.g., DOW CORNING 246 Fluid (d6+ d5)). Silsesquioxane compounds (sometimes referred to as silsesquioxane resins) may also be included in the hair-treatment compositions. For example, in some cases, the hair-treatment compositions may include a polysilsesquioxanes such as, for example, polymethylsilsesquioxane, polypropylsilsesquioxane, polyphenylsilsesquioxane, etc., and a mixture thereof.

Other non-limiting examples of silicones are silicones having side groups or side chains. In some cases, the side groups are hydrophobic. In some cases, the side groups are straight chained, while in other embodiments the side groups are branched. Exemplary side chains include those having 1 to 6, or 2 to 6, or 3 to 6 or 3 to 6 or 5 to 6 carbons or heteroatoms (e.g., O, S, or N) (or a mixture thereof). Exemplary linear side chains include, without limitation, methyl, ethyl, propyl, butyl, pentyl, and hexyl. Exemplary branched side chains include, without limitation, isopropyl, isobutyl, and tert-butyl. In one nonlimiting embodiment, the branched side chain is —O—Si(CH$_3$)$_3$. Nonlimiting examples of silicones having branched side chains are stearyl dimethicone and phyenyltrimethicone, cetyl dimethicone, caprylyl methicone, PEG/PPG 18/18 dimethicone the structures of which are as follows:

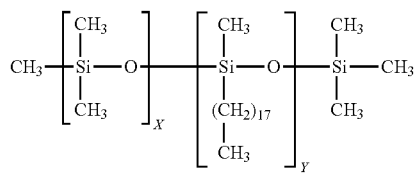

Stearyl Dimethicone

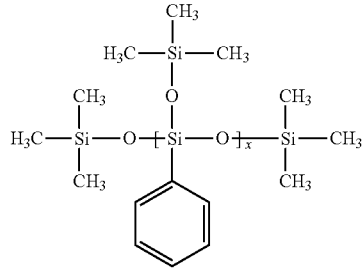

Phenyltrimethicone

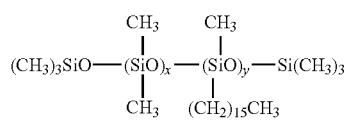

Cetyl Dimethicone

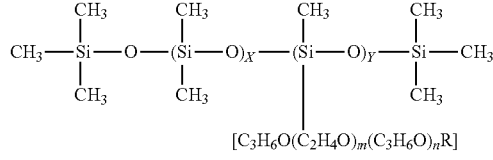

PEG/PPG 18/18 dimethicone

In the above formulas m, n, x, and y may independently be integers of 1 to 100, 1 to 80, 1 to 60, 1 to 50, 1 to 40, 1 to 30, 1 to 20, or 1 to 10. In some cases, the side chains are cyclic. Cyclic side chains include aliphatic side chains and aromatic side chains. A nonlimiting example of a cyclic side chain is phenyl.

With regard to silicones having hydrophilic or polar groups, as described previously, silicones that are repulsive with regard to the hydrophobic chains of the oil are thought to produce more stable foams because they do not inhibit the hydrophobic-hydrophobic interactions of the oil. Exemplary hydrophilic or polar groups include oxygen-containing groups, such as carbonyl groups, hydroxy groups, ether, ester, carboxylic groups, which replace one or more methyl groups. The hydrophilic/polar groups are present alternatively in the main chain of the silicone or in a side chain. Nonlimiting examples of a silicone having a hydrophilic group are PEG/PPG 18/18 dimethicone and dimethiconol, the structures of which are:

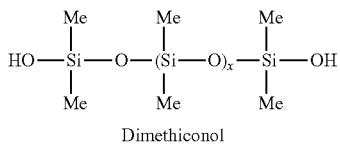

Dimethiconol

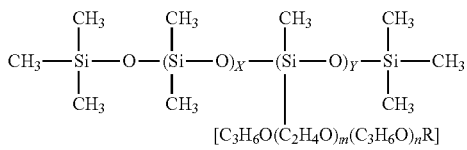

PEG/PEG 18/18 Dimethicone

X, y, m, and n are as defined above, and R is a C$_1$ to C$_{10}$ alkyl.

Another type of specific non limiting volatile silicone is a volatile short chain linear alkylmethylsilicone fluid. The volatile short chain linear alkylmethylsilicone fluid has the formula:

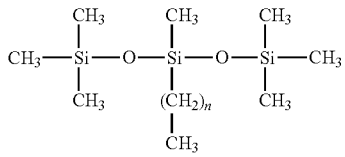

In the above formula, the integer represented by n has a value of five to twelve. Preferably, n has a value of five to eight. Compounds include, for example, 3-hexyl-1,1,1,3,5,5,5,-heptamethyltrisiloxane and 3-octyl-1,1,1,3,5,5,5-heptamethyltrisiloxane.

Yet another type of volatile silicone in accordance with the present invention is a volatile short chain linear phenylmethylsilicone fluid. The volatile short chain linear phenylmethylsilicone fluid has the formula:

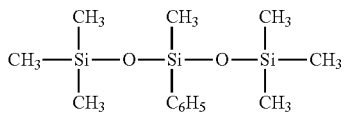

This compound is 3-phenyl-1,1,1,3,4,4,4-heptamethyltrisiloxane. Further volatile silicone fluids useful in the compositions described herein include, without limitation, are decamethylcyclopentasiloxane (DMCPS) which has a molecular weight of about 370, a refractive index of 1.40, and the formula [(Me$_2$)SiO]$_5$; the compound 3-hexyl-1,1,1,3,5,5,5-heptamethyltrisiloxane (HHMTS) which has a molecular weight of about 306, and a refractive index of 1.41; and the compound 3-phenyl-1,1,1,3,5,5,5-heptamethyltrisiloxane (PHMTS) which has a molecular weight of about 298 and a refractive index of 1.45.

As amino silicone that may be used in the scope of the instant disclosure, the following can be cited:

a) polysiloxanes corresponding to formula (A):

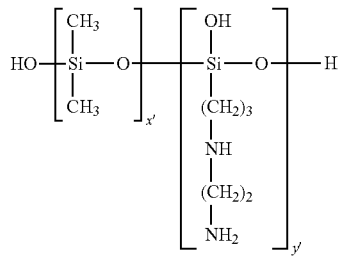

(A)

in which x' and y' are integers such that the weight-average molecular weight (Mw) is comprised between about 5000 and 500 000 b) amino silicones corresponding to formula (B):

(B)

in which:

G, which may be identical or different, designate a hydrogen atom, or a phenyl, OH or $C_1$-$C_8$ alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

R', which may be identical or different, denote a monovalent radical having formula —$C_qH_{2q}L$ in which q is a number ranging from 2 to 8 and L is an optionally quaternized amino group chosen from the following groups:

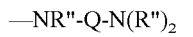

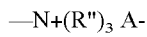

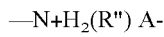

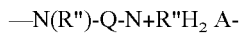

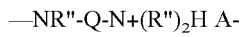

in which R", which may be identical or different, denote hydrogen, phenyl, benzyl, or a saturated monovalent hydrocarbon-based radical, for example a $C_1$-$C_{20}$ alkyl radical; Q denotes a linear or branched $C_rH_{2r}$ group, r being an integer ranging from 2 to 6, preferably from 2 to 4; and A- represents a cosmetically acceptable ion, in particular a halide such as fluoride, chloride, bromide or iodide.

A group of amino silicones corresponding to this definition (B) is represented by the silicones called "trimethylsilylamodimethicone" having formula (C):

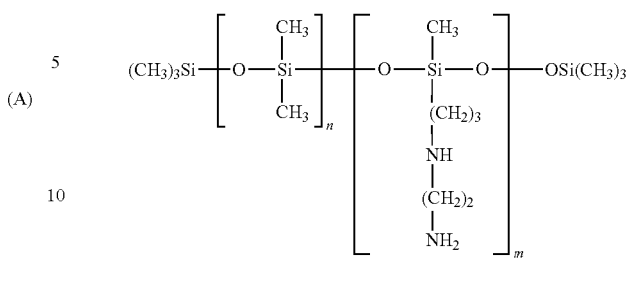

(C)

in which n and m have the meanings given above, in formula B.

Another group of amino silicones corresponding to this definition is represented by silicones having the following formulae (D) or (E):

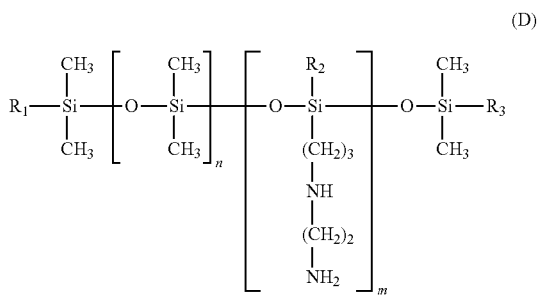

(D)

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and form to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of the silicone ranges preferably from 2000 to 1 000 000, more particularly from 3500 to 200 000.

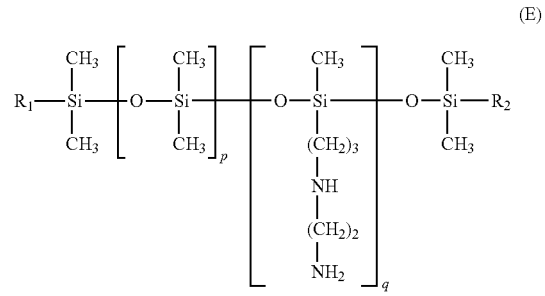

(E)

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which are different, represent a hydroxy or $C_1$-$C_4$ alkoxy radical, where at least one of the radicals $R_1$ or $R_2$ denotes an alkoxy radical.

The alkoxy radical is preferably a methoxy radical.

The hydroxy/alkoxy mole ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200 000, even more particularly 5000 to 100 000 and more particularly from 10 000 to 50 000.

Commercial products corresponding to these silicones having structure (D) or (E) may include in their composition one or more other amino silicones whose structure is different than formulae (D) or (E).

A product containing amino silicones having structure (D) is sold by Wacker under the name Belsil® ADM 652.

A product containing amino silicones having structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometres. Preferably, in particular as amino silicones having formula (E) are used, microemulsions are used whose average particle size ranges from 5 nm to 60 nanometres (limits included) and more preferably from 10 nm to 50 nanometres (limits included). Accordingly, according to the invention the microemulsions of amino silicone having formula (E) sold as Finish CT 96 E® or SLM 28020® by Wacker can be used.

Another group of amino silicones corresponding to this definition is represented by the following formula (F):

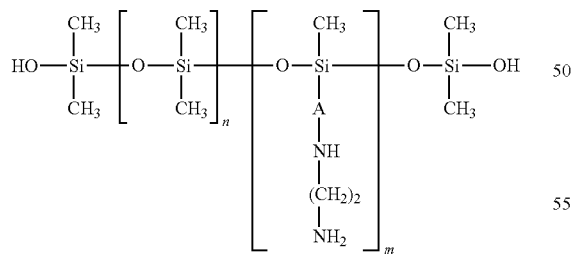

(F)

in which:

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

A preferred silicone of formula (F) is amodimethicone (INCI name) sold under the tradename XIAMETER® MEM-8299 Cationic Emulsion by Dow Corning.

Another group of amino silicones corresponding to this definition is represented by the following formula (G):

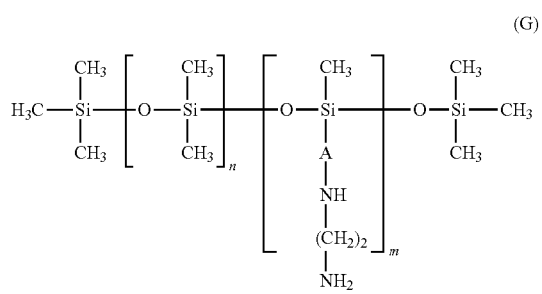

(G)

in which:

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

A silicone having this formula is for example DC2-8566 Amino Fluid by Dow Corning.

c) amino silicones corresponding to formula (H):

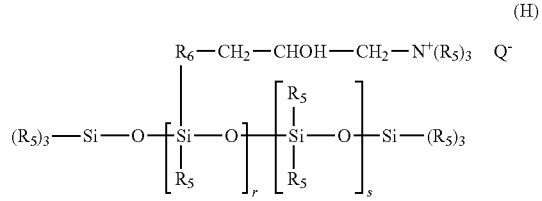

(H)

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q- is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50.

Such amino silicones are described more particularly in U.S. Pat. No. 4,185,087.

d) quaternary ammonium silicones having formula (I):

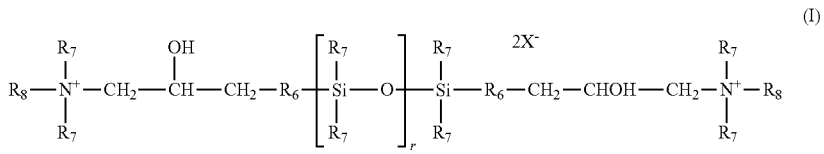

in which:
- $R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;
- $R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—$NHCOR_7$ radical;
- X— is an anion such as a halide ion, in particular chloride, or an organic acid salt (for example acetate);
- r represents a mean statistical value from 2 to 200 and in particular from 5 to 100;

These silicones are described, for example, in patent application EP-A 0 530 974.

e) amino silicones having formula (J):

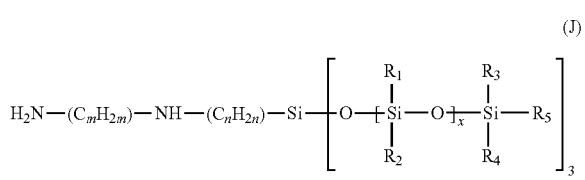

in which:
- $R_1$, $R_2$, $R_3$ and $R_4$, which may be identical or different, denote a $C_1$-$C_4$ alkyl radical or a phenyl group;
- $R_5$ denotes a $C_1$-$C_4$ alkyl radical or a hydroxyl group;
- n is an integer ranging from 1 to 5;
- m is an integer ranging from 1 to 5;
- and in which x is chosen such that the amine number is between 0.01 and 1 meq/g;

f) multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

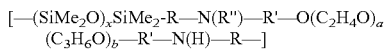

or alternatively

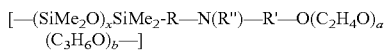

in which:
- a is an integer greater than or equal to 1, preferably ranging from 5 to 200, more particularly ranging from 10 to 100;
- b is an integer comprised between 0 and 200, preferably ranging from 4 to 100, more particularly between from 5 and 30;
- x is an integer ranging from 1 to 10 000, more particularly from 10 to 5000;
- R" is a hydrogen atom or a methyl;
- R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;
- R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably comprised between 5000 and 1 000 000, more particularly between 10 000 and 200 000.

Mention may be made especially of the silicones sold under the names Silsoft™ A-843 or Silsoft™ A+ by Momentive.

g) the alkylamino silicones corresponding to formula (K) below:

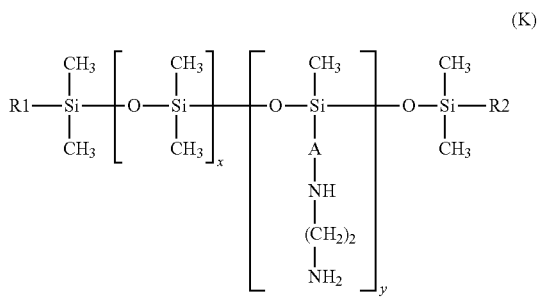

in which:
- x and y are numbers ranging from 1 to 5000; preferably, x ranges from 10 to 2000 and especially from 100 to 1000; preferably, y ranges from 1 to 100;

R₁ and R₂, which may be identical or different, preferably identical, are linear or branched, saturated or unsaturated alkyl radicals, comprising 6 to 30 carbon atoms, preferably 8 to 24 carbon atoms and especially 12 to 20 carbon atoms;

A denotes a linear or branched alkylene radical containing from 2 to 8 carbon atoms, Preferably, A comprises 3 to 6 carbon atoms, especially 4 carbon atoms; preferably, A is branched. Mention may be made especially of the following divalent radicals: —CH₂CH₂CH₂ and —CH₂CH(CH₃)CH₂—.

Preferably, R₁ and R₂, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, R₁ and R₂, which may be identical or different, are chosen from hexadecyl (cetyl) and octadecyl (stearyl) radicals.

Preferentially, the silicone is of formula (K) with:
x ranging from 10 to 2000 and especially from 100 to 1000;
y ranging from 1 to 100;
A comprising 3 to 6 carbon atoms and especially 4 carbon atoms; preferably, A is branched; and more particularly A is chosen from the following divalent radicals: CH₂CH₂CH₂ and —CH₂CH(CH₃)CH₂—; and
R₁ and R₂, which may be identical or different, being linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, R₁ and R₂, which may be identical or different, being chosen from hexadecyl (cetyl) and octadecyl (stearyl) radicals.

A preferred silicone of formula (K) is bis-cetearylamodimethicone (INCI name).

Mention may be made especially of the silicone sold under the name Silsoft™ AX by Momentive.

The amino silicones may be chosen from the amino silicones of formula (F). A preferred silicone of formula (F) is amodimethicone (INCI name) sold under the tradename XIAMETER® MEM-8299 Cationic Emulsion by Dow Corning.

Implementation of the present disclosure is provided by way of the following examples. The examples serve to illustrate the technology without being limiting in nature.

| | | Example 1 | | | | | | | |
|---|---|---|---|---|---|---|---|---|---|
| | | #1 wt. % | #2 wt. % | #3 wt. % | #7 wt. % | #4 wt. % | #8 wt. % | #5 wt. % | #6 wt. % |
| | INCI US | Inventive Examples | | | | Comparative Examples | | | |
| Bis-Urea Derivative | BIS-(C12-14 ALKYL PPG-4) HEXAMETHYLENEDIUREA | 0.5 | 8 | 0.5 | 0.5 | | | | |
| Hydrophobic Silica Aerogel | SILICA SILYLATE | 0.3 | 0.3 | 0.3 | | 0.3 | 0.3 | 0.3 | 0.3 |
| Silcone | CYCLOHEXASILOXANE AND/OR POLYPROPYL- SILSESQUIOXANE | | | 25.7 | 25.7 | | 25.7 | | |
| Film-Forming Polymer | CARBOMER/HYDROXY ETHYL CELLULOSE | | | | | | | 1 | 1 |
| Dilluent(s) (Ester Oils) | C12-15 ALKYL BENZOATE, ISOPROPYL MYRISTATE, ETHYLHEXYL PALMITATE, AND/OR ISONONYL ISONONANOATE | 99.2 | 91.7 | 67.5 | 67.8 | 93.7 | 68 | 93.4 | 93.2 |
| Dilluent (Non- Ester Oil) | ISODODECANE | | | 6 | 6 | 6 | 6 | 6 | 6 |
| | Form | Clear Liquid | Solid (pomade) | Clear Slush | Clear Liquid | Liquid | Clear Liquid | Liquid | Clear Liquid |
| | Stable | Yes | Yes | Yes | Yes | No | No | No | No |
| | Shine | ✓ | ✓ | ✓ | ✓ | X | X | X | X |
| | Easy Blow Dry | ✓ | ✓ | ✓ | ✓ | X | X | X | X |
| | Shape Control | ✓ | ✓ | ✓✓ | ✓ | X | X | X | X |
| | Texture/Feel | ✓ | ✓ | ✓✓ | X | X | X | X | X |
| | Smoothness | — | — | ✓ | ✓ | X | X | X | X |
| | Body | ✓ | ✓ | ✓ | X | X | X | X | X |
| | Frizz Control | ✓ | ✓ | ✓ | ✓ | X | X | X | X |

Formulation #2 was compared to three popular commercial benchmark products that are advertised as products for providing styling benefits and heat protection to hair, especially hair that is blow dried or treated with a heat iron. The inventive composition outperformed all three commercial benchmark products. Specifically, the inventive composition provided hair with more smoothness, a thicker appearance, better shape and holding properties, more shine, and better frizz control.

Evaluators also reported that hair treated with the inventive composition was perceived to dry more quickly than hair treated with the three commercial benchmark products. This is significant because one of the three commercial benchmark products is specifically advertised for reducing drying time. Nonetheless, evaluators reported perceiving that the inventive composition reduced drying time more than the commercial benchmark product (the inventive composition was perceived to reduce drying time more than all three commercial benchmark products).

In an expert analysis study the characteristics of Formulation #2 were compared with a commercial benchmark product. Ten volunteers participated. The inventive formulation was applied to damp hair of ½ the head of each volunteer and the commercial benchmark products was applied to damp hair on the other ½ the head of each volunteer. Both products were combed through the damp hair. The hair was then blow dried and evaluated by experts. The statistically significant results are provided in the table below.

| Attribute | Formulation #1 | Commerical Benchmark |
|---|---|---|
| Type of Styling Product (1-7) | 6.40 | 4.50 |
| Consistency (0-5) | 3.60 | 2.40 |
| Style/Shape Control (1-10) | 4.75 | 3.95 |
| Smooth tactile (0-5) | 3.25 | 2.65 |
| Static (0-5) | 0.20 | 0.65 |
| Repositionable (0-5) | 2.70 | 2.25 |
| Restylable (0-5) | 3.10 | 2.60 |
| Resulting Volume (0-5) | 2.70 | 2.15 |

The hair treated with the inventive formulation was rated as statistically better than hair treated with the commercial benchmark product in terms of type of styling product, consistency, style/shape control, smoothness, less static, repositionable, restylable, and volume. In other attributes, there was no statistical difference between the products (e.g., sensation on hands, wet hair suppleness, etc.). In no case did the inventive composition perform statistically worse than the commercial benchmark. Thus, the data show that hair treated with the inventive formulation was rated statistically better than hair treated with the commercial benchmark with respect to many important and desirable cosmetic properties.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" is equivalent to "mixtures thereof." Throughout the disclosure, the term "a mixture thereof" may be used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included in a mixture). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions can be modified with the "about," meaning within +/−5% of the indicated number.

Some of the various categories of components identified for the hair-treatment compositions may overlap. In such cases where overlap may exist between two or more components, a single overlapping compound does not represent more than one component. For example, a homopolymer of methyl quaternized dimethylaminoethyl methacrylate may be characterized as both a cationic polymer component and a thickening agent component. If a particular hair-treatment composition is described as including both a cationic polymer and a thickening agent, a single homopolymer of methyl quaternized dimethylaminoethyl methacrylate can serve as only the cationic polymer or only the thickening agent (the compound does not serve as both the cationic polymer and the thickening agent in the same composition).

All percentages, parts and ratios herein are based upon the total weight of the compositions of the present invention, unless otherwise indicated.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term "treat," and its grammatical variations, relates to contacting hair with the hair-treatment compositions of the present disclosure.

The term "rinse," in the context of the instant disclosure, is used as customarily understood in the hair-care/hair-treatment art. For example, when a hair-treatment composition (e.g., a shampoo, conditioner, etc.) is "rinsed" from the hair, it is understood that a large portion or most of the hair-treatment composition is removed from the hair. Nonetheless, in many cases, at least a residual amount of the hair-care composition or ingredient(s) from the hair care composition remains in or on the hair. In fact, in some cases, the residual amount of remaining composition or ingredient(s) is at least in part responsible for one or more of the styling benefits imparted to the hair.

A "rinse-off" hair-treatment composition refers to a composition that is rinsed and/or washed with water either after or during the application of the composition onto the hair, and before drying and/or styling the hair. At least a portion, and typically most, of the composition is removed from the hair during the rinsing and/or washing.

The term "stable" as used herein means that the composition does not exhibit phase separation and/or crystallization for a period of time, for example, for at least 1 day (24 hours), one week, one month, or one year.

"Volatile", as used herein, means having a flash point of less than about 100° C.

"Non-volatile", as used herein, means having a flash point of greater than about 100° C.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3 wt. %, less than about 2 wt. %, less than about 1 wt. %, less than about 0.5 wt. %, less than about 0.1 wt. %, or none of the specified material.

The term "essentially anhydrous" or "substantially anhydrous" as used herein, for example, in the context of an "essentially anhydrous hair-treatment composition" or a "substantially anhydrous hair-treatment composition" means that the composition includes less than about 5% by weight of water. Nonetheless, the composition may include less than about 4 wt. %, less than about 3 wt. %, less than about 2 wt. %, less than about 1 wt. %, less than about 0.5 wt. %, less than about 0.1 wt. % of water, less than about 0.05 wt. % water, or less than 0.01 wt. % water.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. An essentially anhydrous hair-treatment composition comprising:
   less than 3 wt. % of water;
   about 0.1 to about 10 wt. % of BIS-(C12-14 alkyl PPG-4) hexamethylenediurea;
   about 0.01 to about 5 wt. % of silica silylate; and
   about 50 to about 99.5 wt. % of consisting of C12-15 alkyl benzoate, isopropyl myristate, ethyl hexyl palmitate and/or isononyl isononanoate ester oils selected from the group consisting of esters of $C_{6-22}$ fatty acids with a monohydric alcohol and/or esters of $C_{6-22}$ fatty alcohols with a monocarboxylic acid,
   wherein all percentages by weight are based on the total weight of the essentially anhydrous hair-treatment composition.

2. An essentially anhydrous hair-treatment composition of claim 1 comprising less than 0.1 wt. % of water, based on the total weight of the essentially anhydrous hair-essentially anhydrous treatment composition.

3. An anhydrous hair-treatment composition comprising:
   about 0.1 to about 10 wt. % of BIS-(C12-14 alkyl PPG-4) hexamethylenediurea;
   about 0.01 to about 5 wt. % of silica silylate; an
   about 50 to about 99.5 wt. % of ester oils selected from the group consisting of C12-15 alkyl benzoate, isopropyl myristate, ethyl hexyl palmitate and/or isononyl isononanoate
   where in all percentages by weight are based on the total weight of the anhydrous hair-treatment composition.

4. A method for treating hair comprising applying a essentially anhydrous hair-treatment composition of claim 1 to the hair.

5. A method for styling hair comprising:
   applying a essentially anhydrous hair-treatment composition of claim 1 to wet or damp hair;
   drying the hair without rinsing the essentially anhydrous hair-treatment composition from the hair.

* * * * *